United States Patent [19]

Maldari et al.

[11] Patent Number: 4,895,446
[45] Date of Patent: Jan. 23, 1990

[54] PARTICLE DETECTION METHOD AND APPARATUS

[75] Inventors: Mario A. Maldari, Stow; Charly Allemand, Newton, both of Mass.

[73] Assignee: Inspex Incorporated, Waltham, Mass.

[21] Appl. No.: 246,464

[22] Filed: Sep. 19, 1988

Related U.S. Application Data

[63] Continuation-in-part of Ser. No. 922,478, Oct. 23, 1986, Pat. No. 4,722,126.

[51] Int. Cl.⁴ .............................................. G01N 15/02
[52] U.S. Cl. ...................................... 356/336; 356/337
[58] Field of Search ............... 356/237, 335, 336, 337; 250/562, 572; 358/107

[56] References Cited

U.S. PATENT DOCUMENTS 4,377,340 3/1983 Green et al. ......................... 356/237
4,772,126 9/1988 Allemand et al. ................... 356/336

*Primary Examiner*—Steven Mottola
*Attorney, Agent, or Firm*—Irving M. Kriegsman

[57] ABSTRACT

An apparatus and method are disclosed for detecting the presence of particles on the surface of an object such as the front side of a patterned semiconductor wafer. A collimated beam of light is directed onto an area on the surface of the object at a grazing angle of incidence. A detector positioned above the surface detects light scattered from any particles which may be present on the surface, but not specularly reflected light. The output of the detector is fed into a computer where the information is processed and then displayed on a display. The surface is prepositioned relative to the incident light beam so that the diffracted light from the surface and the pattern on the surface is at a minimum. The object is then moved translationally to expose another area to the incident light beam so that the entire surface of the object or selected portions thereof can be examined, an area at a time.

6 Claims, 4 Drawing Sheets

PARTICLE DETECTION METHOD AND APPARATUS

CROSS REFERENCE TO RELATED APPLICATION

This application is a continuation-in-part of copending patent application Ser. No. 922,478, now U.S. pat. No. 4,722,126, filed on Oct. 23, 1986 in the names of C.D. Allemand, H. Iida and M.A. Maldari and assigned to Inspex Incorporated, the assignee of this application.

BACKGROUND OF THE INVENTION

The present invention relates generally to a method and apparatus for detecting the presence of contaminant particles on the surface of an object and more particularly to a method and apparatus for detecting and measuring the number and sizes of contaminant particles on the surface of an object using the principle of scattered light.

Although the invention will hereinafter be described specifically in connection with detecting contaminant particles on the front surface of a patterened semiconductor wafer, it is to be understood that the invention may be used in detecting particles on the back surface of a patterned semiconductor wafer as well as surfaces of other objects such as, for example, virgin semiconductor wafers, filmed semiconductor wafers and coated or uncoated aluminum memory discs.

As is known, a patterned semiconductor wafer is a semiconductor wafer in which a plurality of integrated circuits have been formed on its front surface, the individual integrated circuits being usually rectangular in overall area and being arranged in a group or pattern of orthogonal rows and columns. The integrated circuits are eventually cut out from the wafer to form what is commonly referred to as chips.

In the prior art there are a variety of ways for detecting and measuring the number and sizes of particles on a surface of a semiconductor wafer for the purpose of rejecting those wafers which have on their surface one or more particles above certain sizes or for those having on their surface an excessive number of particles.

One of the most prevalent methods employs the human operator using a light field/dark field microscope. Using the eye, the operator actually counts the number of particles and also identifies the size of the particles, such as those between 1 to 20 microns, and then rejects those wafers which have an excessive number of particles or those having particles of or above a certain size. This method is without doubt highly inaccurate and very expensive both in terms of wages for the human operator and in terms of the number of rejects both after the inspection and after production of the chips (when an erroneously passed wafer is found to have an electrical defect, e.g. short circuits, because of the presence of contaminant particles).

In. U.S. Pat. No. 4,377,340 to G.P. Green etc., there is disclosed a method and apparatus for detecting and measuring the number and sizes of impurities on the surface of a material, such as a semiconductor wafer, wherein a beam of high intensity collimated light from a xenon arc lamp is directed onto the surface at normal incidence in the absence of any extraneous light, through a collimating mirror and a pin hole device and whereat the particles will scatter the light, and wherein the surface is viewed by a high light sensitive TV camera which is positioned off-axis to pick up scattered light but not specularly reflected light for display on a viewing screen.

In IBM Technical Disclosure Bulletin Volume 2, No. 10, pages 1672-1673, dated Mar. 1970, there is disclosed a system for detecting repeated geometric defects on a reflecting surface in which a collimated light beam strikes the surface being examined at a infiniate angle of incidence. Light scattered back along the same axis as the angle of incidence is directed through a telescope to a photomultiplier tube.

In IBM Technical Disclosure Bulletin Volume 21, No. 6, pages 2336-2337 dated Nov. 1978, there is disclosed a system for detecting defects on wafers wherein light from a plurality of ring light sources impinges on the wafer at an oblique angle to the wafer surface and wherein light scattered upward from the surface at right angles thereto is fed by a lens system into a broad band array detector.

In U.S. Pat. No. 2,947,212 to R.C. Woods there is disclosed a method of detecting surface conditions on a strip of sheet metal having line markings in which light from a light source is directed toward the surface of the sheet metal in a direction generally perpendicular to the line markings. Non-specular reflection in a selected direction which is perpendicular to the lines, and which is preferably between the angle of incidence and the angle of specular reflection, is monitored by a photoelectric cell which is able to detect a surface flaw by variation in the intensity of the reflected light. The light in the incident beam may be polarized and the light in the selected non-specular reflected beam filtered to pass only such polarized light.

In U.S. Pat. No. 4,342,515 to Akiba et al there is disclosed an inspection apparatus for detecting unfavorable foreign matters existent on the surface of an object such as a semiconductor wafer. The apparatus includes a collimated beam generator portion which projects a collimated beam toward the object to-be-inspected from a side thereof and a mechanism which senses light reflected from the surface of the object, through a polarizer plate. In accordance with the disclosed technique for using the apparatus, the signal-to-noise ratio between a detection signal generated by a pattern of the foreign matter to-be-detected and a signal generated by a normal pattern of the object surface and sensed as a noise component can be enhanced.

In U.S. Pat. No. 3,782,836 to Fey et al there is disclosed a surface irregularity analyzing system which includes structure for directing light toward a surface in a direction having a certain angular relationship to the surface. If the light stikes irregularities in the surface it is reflected in a direction having an angular relationship to the surface other than equal and opposite the incident direction. The amount of light reflected from irregularities in the surface is determined, either photographically or photoelectrically, to provide an analysis or irregularities in the surface.

It is an object of this invention to provide a new and improved method and apparatus for detecting the presence of contaminant particles on a surface of an object or a portion of a surface of an object using the principle of scattered light.

It is another object of this invention to provide a method and apparatus as described above in which the object being examined is the front surface of a patterned semiconductor wafer.

It is still another object of this invention to provide a novel optical arrangment for illuminating an area on a surface for the purpose of detecting light scattered by unwanted particles which may be present on the surface.

It is yet still another object of this invention to provide a method and apparatus for detecting particles on an area of a surface which involves illuminating the area of the surface at a grazing angle of incidence with a collimated beam of light.

It is a further object of this invention to provide a method and apparatus as described above in which the area being examined is imaged in real time and the sensitivity is maximized.

It is another object of this invention to provide a method and apparatus as described above wherein unwanted reflected light from the surface and/or from an integrated circuit pattern which may be present on the surface is reduced to a minimum.

It is still another object of this invention to provide a method and apparatus as described above in which the surface being examined is the front surface of a patterened semiconductor wafer and is illuminated, an area at a time.

It is yet still another object of this invention to provide method and apparatus as described above in which the signal to noise ratio between scattered light from contaminant particles which may be present on the surface and diffracted light from the surface itself or from an integrated circuit pattern formed on the surface is maximized.

It is a further object of this invention to provide a system designed especially for use in dark field illumination applications.

The foregoing and other objects as well as many advantages of the invention will appear from the description to follow. In the description, reference is made to the accompanying drawings which forms a part thereof, and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to taken in a limiting sense, and the scope of the present invention is best defined by the appended claims.

SUMMARY OF THE INVENTION

Apparatus for use in detecting particles on the surface of an object constructed according to the teachings of the present invention comprises a holder for holding the object to be examined, means for moving the holder translationally about two mutually perpendicular axes, means for rotating the holder about an axis perpendicular to the plane defined by the two mutually perpendicular axes, means for illuminating an area on the surface of the object at grazing angle of incidence with a collimated beam of light, means disposed above the object for detecting light scattered from any particles which may be present on the surface, means for processing and/or storing signals corresponding to the light detected and means for displaying an image of the light detected.

A method for detecting particles on the surface of an object according to this invention comprises directing a beam of collimated light onto an area on the surface of the object at a grazing angle of incidence, orienting the surface of the object relative to the incident light beam so that the diffracted light from the surface and/or a pattern that may be formed on the surface is at a minimum, detecting light scattered from the surface, processing signals corresponding to the light so detected and the displaying an image of the light so detected.

BRIEF DESCRIPTION OF THE DRAWINGS

In the drawings wherein like reference numerals represent like parts.

DETAILED DESCRIPTION OF PREFERRED EMBODIMENTS

The present invention is directed to a method and apparatus for detecting the presence of contaminant particles on the surface of an object using the principle of scattered light.

In accordance with the invention an area on the surface to be examined is illuminated with a beam of collimated light at grazing angle of incidence. A grazing angle of incidence is used fro the illuminating light beam in order to improve the signal to noise ratio (the ratio between signals from particles and signals caused by background scatter). A light detector is positioned above the surface of the object. Light scattered by any particles which may be present on the area of the surface that is illuminated is detected by the light detector. Because of the angle at which the incident light beam strikes the surface and the angle at which the light detector is positioned relative to the surface, specularly reflected light from the surface is not picked up by the light detector. The surface is oriented relative to the incident light beam to a position where the diffracted light from the area illuminated is at a minimum and the light detector is angularly positioned relative to the surface to where the diffracted light detected by the light detector is at a minimum. The output of the light detector is processed in a computer and then displayed on a monitor. The object is then moved translationally relative to the incident light beam so that another area can be examined and so forth. Using the invention, contaminant particles on the order of 1 micron and less can be repeatedly detected.

Figure 1:
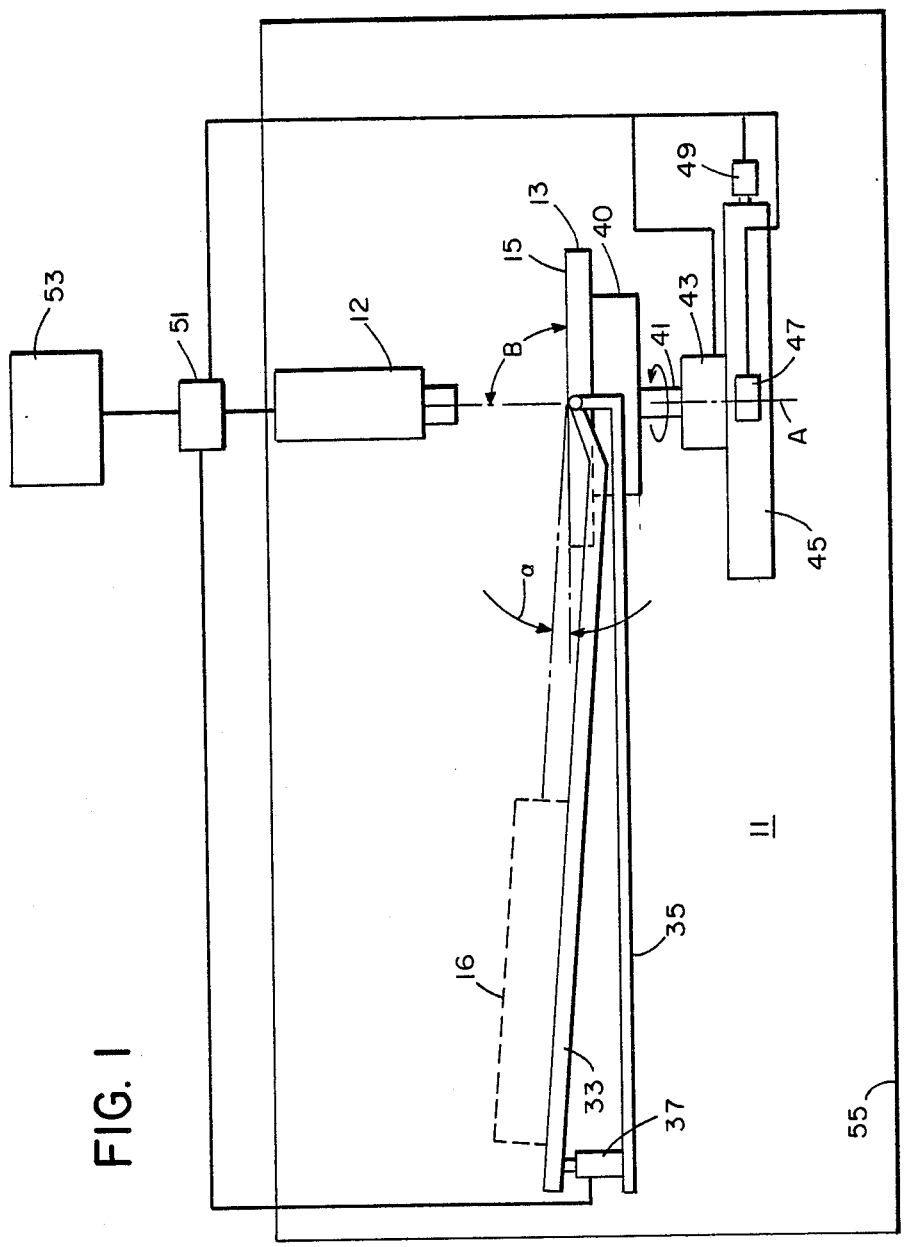
FIG. 1 is a schematic representation of an embodiment of an apparatus constructed according to the teaching of the present invention for detecting the presence of contaminant particles on the surface of an object; the object shown under examination being a patterned semiconductor wafer and the surface under examination being the front surface.

Referring now to the drawings there is illustrated in FIG. 1 an apparatus 11 for use in detecting the presence of particles on the surface of an object according to this invention. Also shown in FIG. 1 is a patterned semiconductor wafer 13. Wafer 13 includes a pattern of integrated circuits 14 on its front surface 15 (see FIG. 2).

Apparatus 11 includes a light beam generating section which is shown in FIG. 1 symbollically as a dotted line rectangle numbered 16 and a light detector 12.

Figure 2:
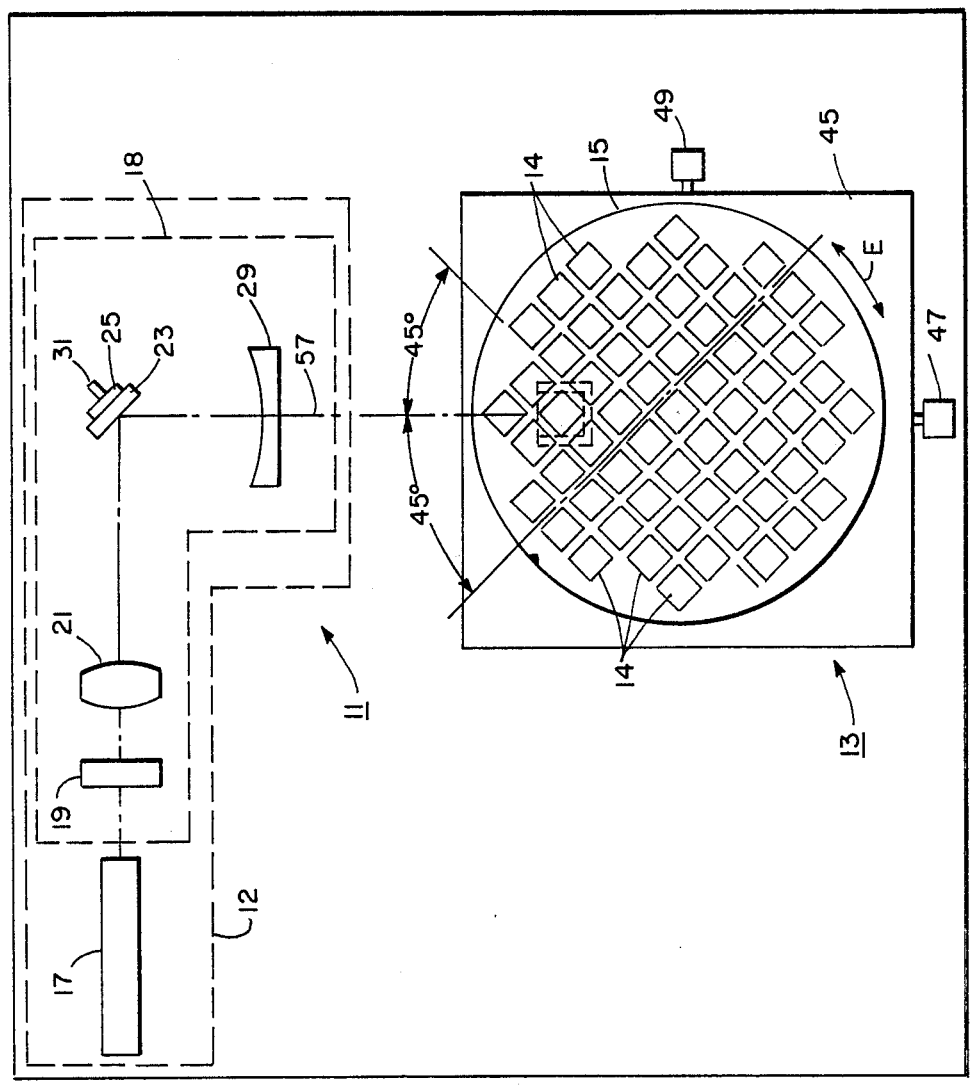
FIG. 2 is a plan view of a portion of the apparatus and wafer shown in FIG. 1 with the patterened semiconductor wafer in palce and in proper orientation, illustrating how the wafer is angularly oriented relative to the incident light beam.

Light beam generating section 16, which is shown in more detail in FIG. 2, includes a laser light source 17, such as a helium-neon laser, for generating a high intensity collimated beam of light and a beam shaping section 18 for shaping the beam of light from laser light source 17 to match the field of view of detector 12. The beam of light produced by light source 17, which is polarized, is circular in cross-section and has a diameter of about 0.8 mm. enters section 18 and is caused to diverge in the vertical direction and remain collimated in the horizontal direction by means of a first cylindrical lens 19. A spherical lens 21 collimates the beam of light passed by first cylindrical lens 19 in the vertical direction so that it has a height of about 2 mm. and causes the beam to converge in the horizontal direction where it is brought to focus on the mirror 23 of a scanning galvanometer 25. The light beam deflected by the scanning galvanometer 25 and which is diverging in the horizontal direction, collimated in the vertical direction and scanning horizontally is passed through a second cylindrical lens 29 which is at a distance from scanning galvanometer 25 equal to its focal length. Second cylindrical lens 29 collimates the light beam in the horizontal direction so that it has a width of about 0.8 mm. while leaving the beam collimated in the vertical direction. Galvanometer scanner 25 includes an adjusting knob 31 which enables the amplitude and hence the distance of the sweep to be varied.

The light beam passed by the second cylindrical lens 29 which is expanded vertically and scanning horizontally so as to define a beam which is generally rectangular in cross-section leaves beam shaping section 16 and is directed onto the top surface 13 of semiconductor wafer 15 at a grazing angle of incidence α (i.e. an angle of between around 0 and 5 degrees), the polarization of the light beam being perpendicular to the plane of incidence and the area on the surface 13 being illuminated by the light beam defined by a rectangle labelled A-B-C-D. As can be appreciated, the intensity of the light striking surface 13 will not be uniform over the entire area A-B-C-D but rather will decrease towards edge CD. Over area E-F-G-H, however, the intensity is relatively uniform.

As can be seen in FIG. 2, semiconductor wafer 13 has a pattern of rectangularly shaped integrated circuits 14 formed on it, the integrated circuits 14 being arranged in spaced orthogonal rows $R_1$, $R_2$, etc. and columsn $C_1$, $C_2$, etc. and aligned with one another. For simplicity, the actual circuit inside each rectangle is not shown. Each circuit 14 has a front edge 14-101, a back edge 14-102 and a pair of side edges 14-103 and 14-104. Also for simplicity, the circuits 14 are not shown in FIG. 1.

In accordance with the invention, when particles are to be detected, semiconductor wafer 13 is positioned so that the incident light beam from light beam generating section 16 strikes the surface at an angle of 45 degrees to the front and back edges 14-101 and 14-102 and at an angle of 45 degrees to the side edges 14-103 and 14-104, as shown, this angular position being where the combined diffracted light from edges 14-101 through 10-104 of the integrated circuits at a minimum. This position also minimizes diffracted light from lines on the individual integrated circuits 14 which are parallel to the edges.

The components making up light beam generating section 12 are fixedly mounted on a bifurcated plate 33 which is hinged at one end to a base 35. A drive mechanism 37 connected between plate 33 and base 35 enables the angle between plate 33 and base 35 and hence the angle of incidence α of the light beam to be selectively varied. Base 35 is supported on a frame (not shown).

Light detector 12 is a high sensitivity video camera, such as model C1000-12 manufactured by Hamamatsu TV Co. Ltd of Japan and is positioned above wafer 13 at an angle B, which is in the vicinity of 90 degrees, for detecting light scattered from surface 15, the exact angle B being where the diffracted light received by camera 39 is at a minimum.

Wafer 13 is seated on a holder 40 which is in the form of a vacuum chuck. Holder 40 is mounted on a vertical shaft 41 which is rotable about its longitudinal axis A by means of a motor 43 so that wafer 13 can be rotated relative to the incident light beam to the angular position noted above where the diffracted light is at a minimum. Motor 43 is mounted on a platform 45 which is movable translationally in two mutually perpendicular direction by two stepping drive motors 47 and 49 so that the entire surface of wafer 13 can be illuminated, an area at a time, by the impinging beam of light.

Camera 12 is connected to a (digital) computer 51 which is coupled to a monitor or display 53. Computer 51 includes an analog to digital converter 52 for digitizing the output of video camera 12 and a programmable memory for storing information concerning predetermined specific areas within the field of view and under illumination from which signals received by camera 12 should be ignored (i.e. not displayed on monitor) because they are not scattered light from contaminant particles. The entire apparatus 11, except for computer 51 and display 53 is preferably enclosed within a light tight housing 55 to eliminate stray light.

Drive mechanism 37, motors 43, 47 and 49, light beam generating section 12, camera 12 and display 53 are all controlled by computer 51.

Apparatus 11 is used in the following manner. A wafer 13 to be examined is placed on holder 40 and camera 12 brought to focus over area E-F-G-H of area A-B-C-D where the intensity of the incident light is uniform. Wafer 13 is then rotated about an axis perpendicular to the plane of the wafer (by rotating holder 40 about axis A), as shown by arrow E in FIG. 2 to the angular position as shown in FIG. 2 where the edges of the integrated circuits 14 are at 45 degrees relative to the incident light beam 57 so that the diffracted light from the edges of the integrated circuits as well as any lines in the individual circuits parallel to these edges is at a minimum. Also, plate 33 is angularly adjusted to a grazing angle where the diffracted light received by camera 39 is minimized and camera 39 tilted to the angle B where the diffracted light is at a minimum.

With wafer 13 at the optimum angular position as shown in Fig. 2 and stationary, the area A-B-C-D is illuminated by light beam generating section 16. The light scattered from that area within area E-F-G-H is detected by camera 12.

The area being examined need only be scanned (i.e. swept by the galvanometer) a single time. However, the background scatter can be reduced and thus the signal to noise ratio (between background scatter and particle scatter) improved by taking multiple scans rather than a single scan and integrating the results, since the background scatter will tend to shift slightly from reading to reading while the particle scatter remains fixed.

The signal to noise ratio can be further improved by taking readings at two different grazing angles such as 4 degrees and 1 degree, adjusting the signals received so that the background signals are equal and then subtracting the signal at the larger angle from the signal at the smaller angle. As can be appreciated, the background signals will cancel out while the particle signals will not cancel out. This is because the background signal decreases faster than the particle signal as the angle of illumination is decreased. For example, at a 4 degree angle of illumination the background signal may be 200 units and the particle signal 100 units while at a 1 degree angle of illumination the background signal may decrease to 20 units while the particle signal decreases to 50 units. If the two 4 degree signals are divided by ten (so that the background signal is the same number as the 1 degree signal) and then the two 4 degree signal subtracted from the two 1 degree signal, the two background signals will cancel out while the particle signal becomes 40 units.

The output of camera 12 is fed into computer 51 where it is digitized and processed.

Figure 2A:
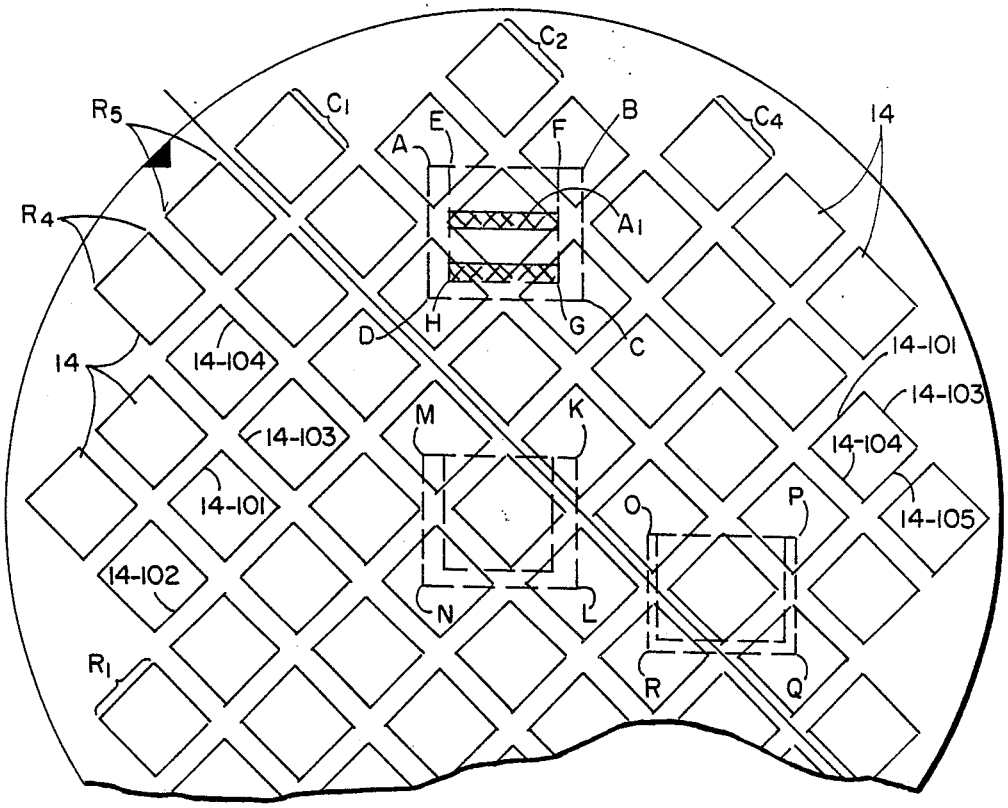
FIG. 2(a) is an enlarged view of a portion of the wafer shown in FIG. 2.

The processing in computer 51 includes ignoring (i.e. discarding) signals received from preselected areas within the field of view under examination. The preselected areas are areas where it has been previously determined that the background signals are too high or, in other words, that the signals detected are background scatter and not particle scatter. Two such areas are shown in FIG. 2(a) and labelled $A_1$ and $A_2$. The background signals may be caused, for example, by lines within the actual integrated circuits not parallel to the edges of the integrated circuits or some specific areas within the integrated circuit which produces high background scatter not corrected by positioning the wafer as discussed above. The preselected areas are determined by examining an area of properly oriented particle-free wafer having a pattern corresponding to the pattern of the wafer under examination. Once the preselected areas within the area under examination to be ignored are determined, the information corresponding to those areas is fed into the computer 51.

The information processed in computer 51 is then displayed on display 53. Wafer 13 is then moved translationally so that other areas on surface 13 such as are KLMN and OPQR may be examined, an area at a time, as desired.

Figure 3:
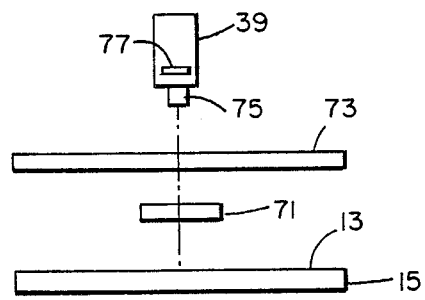
FIG. 3 shows a modification of a portion of the apparatus shownin FIG. 2.

In FIG. 3 there is shown a modification of the readout portion of the apparatus in which the diffracted light from surface 15 and the pattern of lines on surface 15 is further mimimized. A lens 71 disposed above surface 15 forms a Fourier transform of surface 15 on a mask 73. Mask 73 contains a pattern corresponding to the Fourier transform of the patterned surface. Thus, all of the light from surface 13 but not light scattered from any particles on the sruface will be masked off. Lens 75 of camera 39 images surface 13 on the target 77 of camera 39

Figure 4:
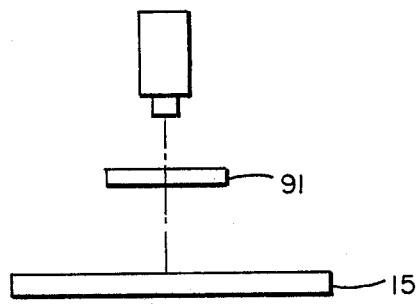
FIG. 4 shows still another modification of a portion of the apparatus shown in FIG. 2.

In still another modification of the invention, which is shown in FIG. 4, the signal-to-noise ratio between scattered light and background light is further improved by positioning a polarizer 91, which is cross-polarized relative to the polarization of the incident light beam, in front of camera 39.

Figure 5:
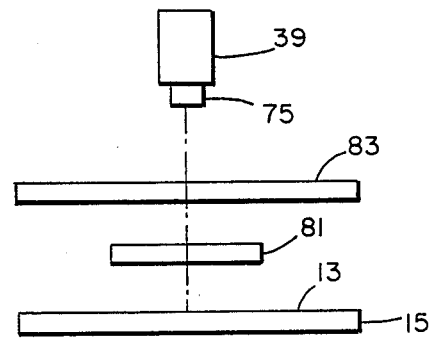
FIG. 5 shows a further modification of a portion of the apparatus shown in FIG. 2.

In a further modification shown in FIG. 5 a lens 81 forms an image of surface 13 on mask 83. Mask 83 contains a pattern corresponding to all predetermined unwanted light. Objective lens 75 of camera 39 is brought to focus on mask 81 over an area of interest.

Figure 6:
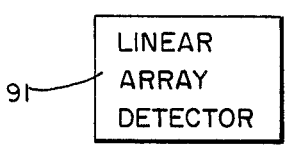
FIG. 6 is a view of a modification of a portion of the apparatus shown in FIG. 2.
Figure 7:
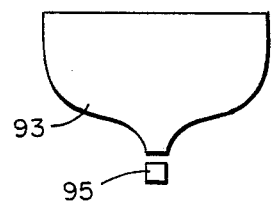
FIG. 7 is a view of another modification of a portion of the apparatus shown in FIG. 2.

In another embodiment of the invention, beam expander elements 19, 21 and 29 are eliminated and detector 12 is replaced by a light detector 91 having a line array of photodiodes. Detector 91 is shown in block diagram form in FIG. 6. In still another embodiment of the invention, elements 19, 21 and 29 are eliminated and detector 12 is replaced by a fiber optic bundle 93 and a single photodetector 95, which may be, for example, a photomultiplier tube or a photodiode, as shown in FIG. 7.

The embodiments of the present invention are intended to be merely exemplary and those skilled in the art shall be able to make numerous variations and modifications to it without departing frm the spirit of the present invention. For example, instead of being expanded vertically and scanning horizontally, the impinging light beam could be expanded horizontally and made scanning vertically. All such variations and modifications are intended to be within the scope of the present invention as defined in the appended claims.

What is claimed is:

1. Apparatus for detecting particles on the front surface of a patterned semiconductor wafer comprising:
    a. holder for holding said semiconductor wafer,
    b. means for illuminating an area on said surface at grazing angle of incidence with a collimated beam of light,
    c. a means for orienting the surface so that light diffracted from the surface and the pattern thereon can be reduced to a minimum,
    d. light detector means disposed above said surface at an angle in the vicinity of ninety degrees to detect light scattered from the area on the surface by any particles thereon and not specularly reflected light and producing signals representative thereof,
    e. a computer for processing signals received by the light detector means,
    f. a display for displaying the processed signals, and
    g. means for moving the holder translationally about two axes so that other areas can be examined.

2. A method of detecting particles on a surface of a semiconductor wafer having a printed circuit pattern thereon comprising:
    a. directing a collimated beam of light onto an area of the surface at a first grazing agnel of incidence,
    b. orienting the semiconductor wafer to a position wherein light diffracted from the surface and from the pattern on the surface is at a minimum, and
    c. detecting the scattered light but not specularly reflected light from at least a portion of said area of said surface that is illuminated and producing electrical signals representative thereof, and
    d. processing said electrical signals, said processing including ignoring signals from preselected places within said area, and
    e. displaying the processed signals.

3. The method of claim 2 and further including repeating steps (a) through (3) for another area on the surface.

4. The method of claim 2 and wherein said collimated beam of light is scanning.

5. The method of claim 4 and wherein the area is scanned a plurality of times and the processing in the computer includes integrating the signals received from the plurality of scans.

6. The method of claim 2 and further including illuminating the area at a second grazing angle of incidence and the processing includes subtracting the signal at the larger angle of incidence from the signal at the smaller angle of incidence.

* * * * *